(12) United States Patent
Hwang et al.

(10) Patent No.: US 12,151,018 B2
(45) Date of Patent: Nov. 26, 2024

(54) COMPOSITION FOR INHIBITING RELEASE OF NEUROTRANSMITTERS

(71) Applicant: LG HOUSEHOLD & HEALTH CARE LTD., Seoul (KR)

(72) Inventors: Woo-Seon Hwang, Seoul (KR); Yun-Sun Kim, Seoul (KR); Mu-Hyun Jin, Seoul (KR); Nae-Gyu Kang, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 686 days.

(21) Appl. No.: 17/432,768

(22) PCT Filed: Feb. 20, 2020

(86) PCT No.: PCT/KR2020/095007
§ 371 (c)(1),
(2) Date: Oct. 29, 2021

(87) PCT Pub. No.: WO2020/171682
PCT Pub. Date: Aug. 27, 2020

(65) Prior Publication Data
US 2022/0142908 A1    May 12, 2022

(30) Foreign Application Priority Data

Feb. 22, 2019 (KR) .................. 10-2019-0021265
Jan. 8, 2020 (KR) .................. 10-2020-0002573

(51) Int. Cl.
*A61K 8/9789* (2017.01)
*A61Q 19/08* (2006.01)

(52) U.S. Cl.
CPC ............ *A61K 8/9789* (2017.08); *A61Q 19/08* (2013.01)

(58) Field of Classification Search
None
See application file for complete search history.

(56) References Cited

U.S. PATENT DOCUMENTS

| | | | |
|---|---|---|---|
| 2011/0112181 A1 | 5/2011 | Kweon et al. | |
| 2012/0021082 A1 | 1/2012 | Artaria et al. | |
| 2012/0258059 A1* | 10/2012 | Iwama | A61K 8/64 424/59 |
| 2015/0342854 A1 | 12/2015 | Shibuya et al. | |
| 2018/0071208 A1 | 3/2018 | Shim et al. | |
| 2018/0222878 A1 | 8/2018 | Kweon et al. | |

FOREIGN PATENT DOCUMENTS

| | | |
|---|---|---|
| CN | 106377449 A | 2/2017 |
| CN | 106963820 A | 7/2017 |
| CN | 107427474 A | 12/2017 |
| CN | 107854355 A | 3/2018 |
| JP | 2003-342184 A | 12/2003 |
| JP | 2012-518607 A | 8/2012 |
| JP | 2012-240971 A | 12/2012 |
| JP | 2017-19754 A | 1/2017 |
| JP | 2019-77643 A | 5/2019 |
| KR | 10-2008-0056576 A | 6/2008 |
| KR | 10-2008-0082955 A | 9/2008 |
| KR | 10-2008-0083438 A | 9/2008 |
| KR | 10-0859950 B1 | 9/2008 |
| KR | 10-0883757 B1 | 2/2009 |
| KR | 10-2011-0017599 A | 2/2011 |
| KR | 10-2011-0120897 A | 11/2011 |
| KR | 10-2015-0103138 A | 9/2015 |
| KR | 10-2016-0080476 A | 7/2016 |
| KR | 10-2017-0091554 A | 8/2017 |
| KR | 10-2017-0119871 A | 10/2017 |

OTHER PUBLICATIONS

Wang, Y. et al. "Botulinum toxin as a cosmetic weapon", Chinese Journal of New Drugs, 2004, vol. 13 No. 12, pp. 1417-1420.
"[Ebury Peptide Cream]/Anti-wrinkle/wrinkle improvement cosmetic", Naver Blog, https://blog.naver.com/1n1q83/90171599681, Apr. 20, 2013, total 14 pages.
Donald et al., "Acute pain relief effect of essential oil from the leaves of *Zanthoxylum piperitum* (L.) DC.(Rutaceae) through glutamatergic pathway", 8th Brazilian Symposium on Essential Oils—International Symposium on Essential Oils, Nov. 10-13, 2015, Rio de Janeiro Botanical Garden, Rio de Janeiro, Brazil total 2 pages.
International Search Report for PCT/KR2020/095007 mailed on Jun. 16, 2020.

* cited by examiner

*Primary Examiner* — Robert A Wax
*Assistant Examiner* — Quanglong N Truong
(74) *Attorney, Agent, or Firm* — Birch, Stewart, Kolasch & Birch, LLP

(57) ABSTRACT

The present disclosure relates to a composition for inhibiting neurotransmitter secretion by inhibiting membrane potential generation of the nerve. The composition of the present disclosure has a synergistic effect related to inhibition of SNARE complex formation, and thereby, it can prevent active secretion of neurotransmitters, and thus can reduce muscle contraction to improve skin wrinkles.

9 Claims, 5 Drawing Sheets

[FIG. 1]
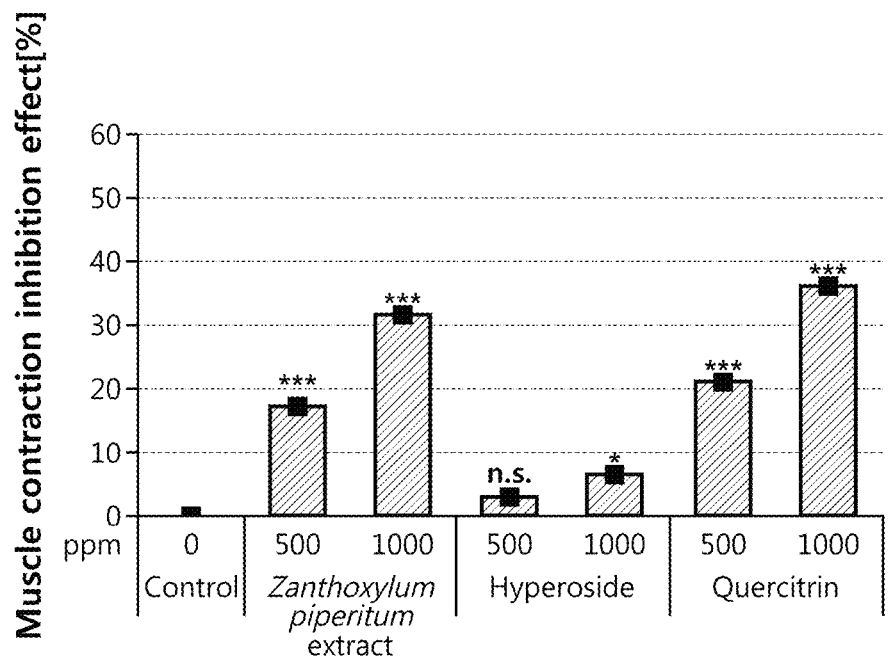
[FIG. 2]
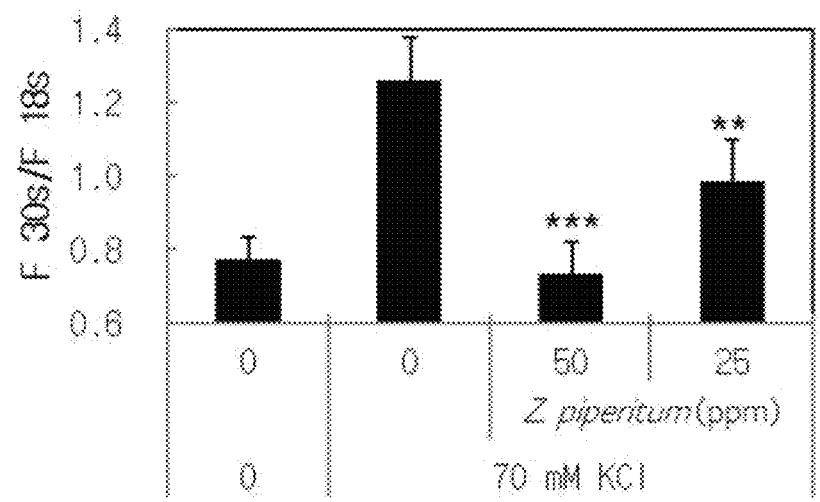

[FIG. 3]
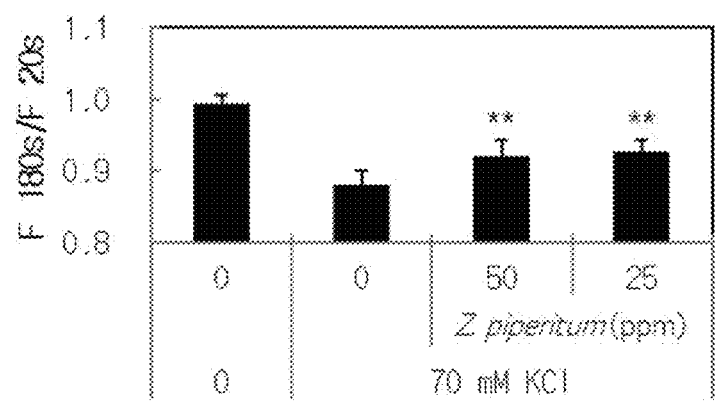
[FIG. 4]
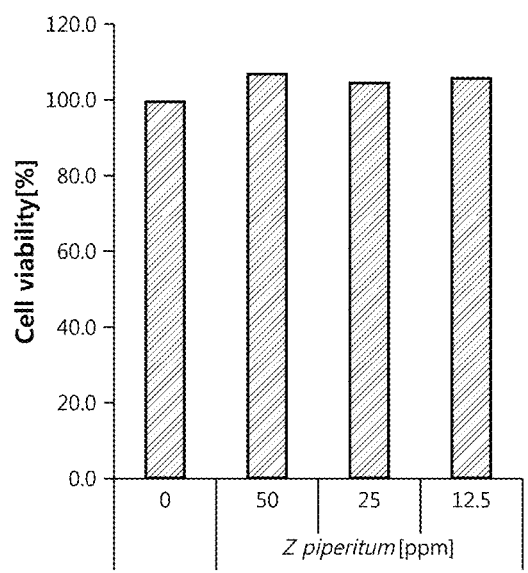

[FIG. 5]
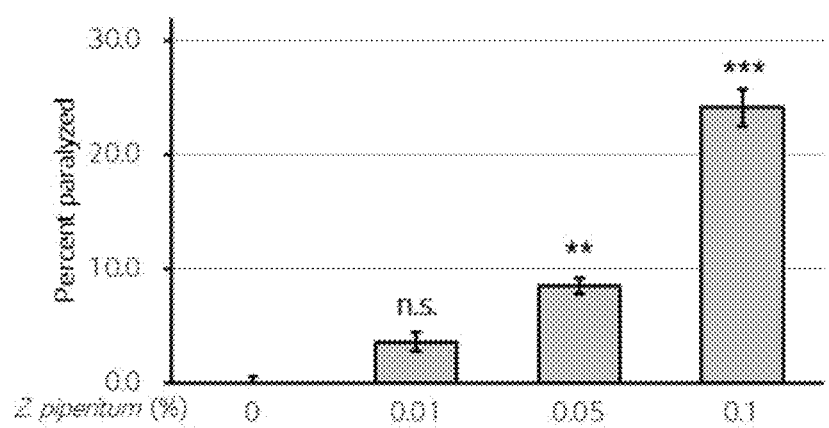

[FIG. 6]
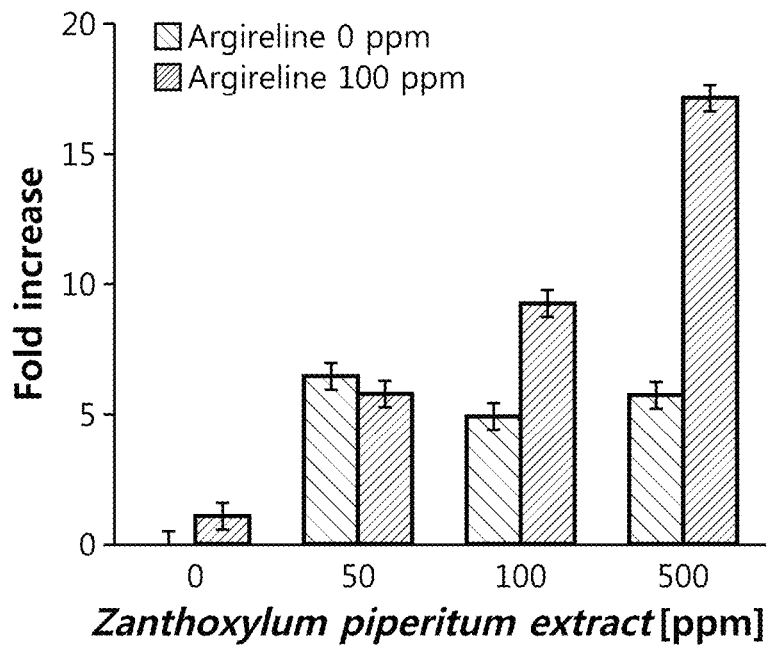
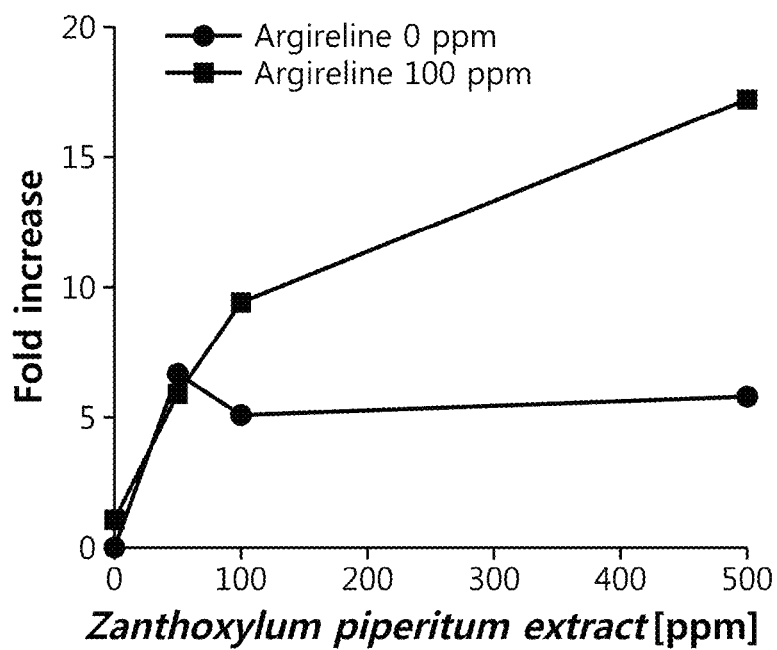

COMPOSITION FOR INHIBITING RELEASE OF NEUROTRANSMITTERS

TECHNICAL FIELD

The present application claims the priority based on Korean Patent Application No. 10-2019-0021265 filed on Feb. 22, 2019 and Korean Patent Application No. 10-2020-0002573 filed on Jan. 8, 2020, and the entire contents disclosed in the description and drawings of the corresponding applications are incorporated in the present application.

The present disclosure relates to a composition for inhibiting neurotransmitter secretion by inhibiting membrane potential generation of the nerve, and a cosmetic composition for improving skin wrinkles comprising the same.

BACKGROUND ART

Aging is a phenomenon in which body functions and abilities deteriorate over time, and is a universal phenomenon that occurs in most living things including humans. The increase in skin wrinkles is one of notable changes among external changes that occur with aging. With aging, wrinkles increase throughout the face and body, and not only aging but also skin moisture, UV exposure and repetitive muscle movements, and the like are involved in formation of wrinkles. Deep wrinkles often occur on the forehead, around the eyes and around the mouth, which move muscles a lot, and wrinkles generated by repetitive muscle movements or facial expressions are called facial wrinkles.

Botulinum toxin is a neurotoxic protein produced by *Clostridium botulinum* bacteria. Botulinum toxin acts at the neuromuscular junction to paralyze muscles by inhibiting the secretion of acetylcholine, a neurotransmitter, from nerve cells. In order for acetylcholine to be secreted from nerve cells, a SNARE complex must be formed at the axon terminal, but botulinum toxin (serotype A) cleaves SNAP-25, one of constituent proteins of the SNARE complex, to prevent the formation of the SNARE complex and consequently inhibit the secretion of acetylcholine.

Botulinum toxin is effective in improving wrinkles by paralyzing muscles. Recently, botulinum toxin has been popularly widely used for cosmetic purposes, but since it is a powerful poison with a half lethal dose of only 10 ng/kg, there are risks of safety accidents, and because it can only be performed by a specialist it cannot be easily accessed by consumers. In addition, there is a disadvantage that an invasive procedure is absolutely necessary for the procedure. In order to secure these shortcomings, there is a need to develop a Botox-like effective material that has low side effects and can be applied to cosmetics and external preparations, and the like.

Throughout the description, numerous documents are referenced and citations thereof are indicated. The disclosures of the cited documents are incorporated herein by reference in their entirety to more clearly describe the level of the art to which the present disclosure pertains and the content of the present disclosure.

DISCLOSURE

Technical Problem

The present inventors have studied and tried to develop a Botox-like effective substance which can inhibit neurotransmitter secretion without any side effects, and as a result, have found that neurotransmitter secretion inhibition and wrinkle improvement can be significantly improved, compared to using each raw material individually, when combining *Zanthoxylum piperitum* fruit extract among other various natural raw materials with a SNARE formation inhibitor, thereby completing the present disclosure.

Accordingly, an object of the present disclosure is to provide a composition for inhibiting neurotransmitter secretion comprising a combination of a *Zanthoxylum piperitum* fruit extract and a SNARE formation inhibitor as an active ingredient.

Another object of the present disclosure is to provide a cosmetic composition and cosmetics for improving skin wrinkles comprising the composition.

Other objects and advantages of the present disclosure will become more apparent from the following detailed description of the invention, claims and drawings.

Technical Solution

An aspect of the present disclosure provides a composition for inhibiting neurotransmitter secretion, comprising a combination of (i) a *Zanthoxylum piperitum* fruit extract and (ii) a SNARE formation inhibitor as an active ingredient.

*Zanthoxylum piperitum* is traditionally a plant with mild nerve stimulation with local anesthetic and analgesic effects, and dried leaves, stems or fruits are used. Extracts from leaves, stems or fruits of *Zanthoxylum piperitum* are known to have mainly antibacterial, antiviral, antiallergic, analgesic and UV protection effects.

The composition of the present disclosure comprises a combination of (i) a *Zanthoxylum piperitum* fruit extract and (ii) a SNARE formation inhibitor as an active ingredient, and the 'extract' used herein has the meaning of including extraction results obtained by squeezing the raw material or treating an extraction solvent to the raw material, or processed products obtained by formulating (e.g., powdering) them.

When the extract used in the composition of the present disclosure is obtained by treating an extraction solvent to the raw material, various extraction solvents may be used, and for example, a polar solvent or non-polar solvent may be used. As the polar solvent, (i) water, (ii) alcohol (preferably, methanol, ethanol, propanol, butanol, normal-propanol, iso-propanol, normal-butanol, 1-pentanol, 2-butoxyethanol or ethylene glycol), (iii) acetic acid, (iv) DMF (dimethylformamide) and (v) DMSO (dimethyl sulfoxide), and the like may be used, and as the non-polar solvent, acetone, acetonitrile, ethyl acetate, methyl acetate, fluoroalkane, pentane, hexane, 2,2,4-trimethylpentane, decane, cyclohexane, cyclopentane, diisobutylene, 1-pentene, 1-chlorobutane, 1-chloropentane, o-xylene, diisopropyl ether, 2-chloropropane, toluene, 1-chloropropane, chlorobenzene, benzene, diethyl ether, diethyl sulfide, chloroform, dichloromethane, 1,2-dichloroethane, aniline, diethylamine, ether, carbon tetrachloride and THF, and the like may be used.

Preferably, the extract used herein may be extracted by squeezing the raw material or using an ultrasonic extractor, or be extracted by using any one selected from the group consisting of water, a lower alcohol having 1 to 4 carbon atoms and a mixture thereof as an extraction solvent, but not limited thereto. More specifically, the extract used herein is an ethanol or ethanol aqueous solution extract of the *Zanthoxylum piperitum* fruit.

In addition, the term used herein, 'extract' has the meaning commonly used as a crude extract in the art as described above, but in a broad sense, also includes a fraction obtained by additional fractionation of the extract. In other words, it includes not only the extract obtained by squeezing the raw material or using the aforementioned extraction solvent, but also one obtained by additionally applying a purification process thereto. For example, a fraction obtained by passing the extract through an ultrafiltration membrane having a constant molecular weight cut-off value, and a fraction obtained through additionally performed various purification methods such as separation by various chromatography (prepared for separation according to the size, charge, hydrophobicity or affinity) are included in the extract of the present disclosure.

Furthermore, the extract of the present disclosure may be obtained by performing an additional process, for example, removing a solvent by performing a filtrating or concentrating or drying process, or performing all of filtrating, concentrating and drying. Filtrating, for example, may use filter paper or use a decompression filter, and concentrating may use a decompression concentrator, and drying may obtain a powdered extract by spray drying or freeze-drying, or the like.

According to one embodiment of the present disclosure, the *Zanthoxylum piperitum* fruit extract prepared as above may comprise quercitrin of 3 to 50 ppm, and preferably, may comprise quercitrin of 4 ppm or more, 5 ppm or more, 6 ppm or more, 7 ppm or more, 8 ppm or more, 9 ppm or more, 10 ppm or more, 11 ppm or more, 12 ppm or more, 13 ppm or more, 14 ppm or more, 15 ppm or more, 16 ppm or more, 17 ppm or more, 18 ppm or more, 19 ppm or more, 20 ppm or more, 30 ppm or more, 40 ppm, or more or 50 ppm.

The SNARE formation inhibitor comprised in the composition of the present disclosure includes substances known as a substance which cleaves a SNARE protein that plays a core action to open a neurotransmitter release passage or makes a SNARE complex unstable in the art, for example, compounds disclosed in Korean Patent No. 10-0883757, but not limited thereto. Specifically, the SNARE formation inhibitor comprised in the composition of the present disclosure may be one or more selected from the group consisting of argireline, botulinum neurotoxin type A light chain (BoNT/A LC), kaempferol, quercetin, myricetin, luteolin, delphinidin, cyanidin, butein and ellagic acid.

The *Zanthoxylum piperitum* fruit extract and SNARE formation inhibitor described above may be comprised as a mixture or complex in the composition of the present disclosure. The mixture or complex is characterized by having a synergistic effect compared to each single substance of the *Zanthoxylum piperitum* fruit extract and SNARE formation inhibitor. More specifically, to show the synergistic effect, the weight of the *Zanthoxylum piperitum* fruit extract comprised in the total composition should be equal to or greater than the weight of the SNARE formation inhibitor.

According to the 'Guidelines for Labeling Full Ingredients in Cosmetics' in Korea, for the ingredients of 1% or more, it is stipulated to list the most contained ingredients first in the order of content.

Article 6 (Order of Labeling): Labeling of ingredients shall be disclosed in the order of content used in cosmetics starting with the most. However, mixed raw materials are indicated as individual ingredients, and ingredients, flavoring agents and coloring agents used at 1% or less may be described in any order.

Argireline, the so-called "appliable Botox", has been used in conventional wrinkle-improving cosmetics for less than 1% of the total weight or in trace amounts, but such small amounts of argireline has little effect. Argireline, as a synthetic peptide, is expensive, so it is disadvantageous in price to use argireline more than 1% of the total weight of the cosmetic product and high concentrations of the substance may lead to side effects. Some conventional wrinkle-improving cosmetics include *Zanthoxylum piperitum* fruit extract and argireline, but in these cases trace amounts of *Zanthoxylum piperitum* fruit extract is comprised as a concept substance along with other natural plant extracts such as rosemary leaf extract, green tea extract, or the like.

However, according to the findings of the present inventors, a synergistic effect appears only when the content of *Zanthoxylum piperitum* fruit extract is more or at least the same as the content of argireline, in the composition. If the content of *Zanthoxylum piperitum* fruit is less than argireline, the synergistic effect does not appear. (See FIG. 6)

In one embodiment, the composition for inhibiting neurotransmitter secretion of the present disclosure may comprise (i) 100 to 500 ppm of the *Zanthoxylum piperitum* fruit extract and (ii) 10 to 100 ppm of the SNARE formation inhibitor, in which the weight of the comprised *Zanthoxylum piperitum* extract is equal to or greater than the weight of the SNARE formation inhibitor. Herein, ppm means the number of mg (or mg/kg) of the substance contained in 1,000,000 mg of the total weight of the composition.

In another embodiment, the content of the *Zanthoxylum piperitum* fruit extract comprised in the composition for inhibiting neurotransmitter secretion of the present disclosure may be 100 ppm or more, 200 ppm or more, 300 ppm or more, 400 ppm or more, 500 ppm or more, 600 ppm or more, 700 ppm or more, 800 ppm or more, 900 ppm or more, or 1000 ppm or more, and the content of the SNARE formation inhibitor may be 10 ppm or more, 20 ppm or more, 30 ppm or more, 40 ppm or more, 50 ppm or more, 100 ppm or more, 200 ppm or more, 300 ppm or more, or 400 ppm or more, but the content of the SNARE formation inhibitor does not exceed the content of the *Zanthoxylum piperitum* fruit extract.

As described above, the composition of the present disclosure in which the *Zanthoxylum piperitum* fruit extract is comprised in more or at least the same amount as the SNARE formation inhibitor such as argireline, has a synergistic effect related to the inhibition of SNARE complex formation, and thus it makes it impossible to actively secrete neurotransmitters, so muscle contraction is less likely to occur, which improves skin wrinkles. The present disclosure provides a cosmetic composition for improving skin wrinkles comprising a combination of the *Zanthoxylum piperitum* fruit extract and the SNARE formation inhibitor based on the effect of the substantially wrinkle-relieving effect.

The cosmetic composition of the present disclosure shows Botox-like efficacy, and the Botox-like efficacy means wrinkle improvement, lifting, sebum secretion improvement, acne improvement, sweat secretion inhibition (hyperhidrosis improvement), improving sagging skin under the eyes, fat under eyes, muscle relaxation and pain relief, and migraine improvement.

When the cosmetic composition is used as a skin external preparation, it may further contain an adjuvant commonly used in the skin science field such as a fat substance, an organic solvent, a solubilizer, a concentrate and a gelling agent, a softener, an anti-oxidant, a suspending agent, a stabilizer, a foaming agent, an air freshener, a surfactant, water, an ionic or non-ionic emulsifier, a filling agent, a metal ion sequestering agent and a chelating agent, a preservative, a vitamin, a blocking agent, a wetting agent, an essential oil, a dye, a pigment, a hydrophilic or lipophilic activator, a lipid follicle or any other components commonly used in the external preparation. In addition, the above ingredients may be introduced in a commonly used amount in the skin science field.

When the composition for improving wrinkles is provided as a skin external preparation, it may have a formulation such as, but not limited thereto, an ointment, a patch, gel, cream or a spray.

In addition, the composition for improving wrinkles of the present disclosure may be used for preparation of cosmetics. When the composition is used as cosmetics, it may be prepared in a form of common emulsion and solubilization formulation. For example, it may have a formulation of cosmetic water such as flexible cosmetic water or nutrient cosmetic water, emulsion such as facial lotion and body lotion, cream such as nutrition cream, moisture cream and eye cream, essence, cosmetic ointment, spray, gel, pack, sun screen, makeup base, a liquid type, solid type or spray type of foundation, powder, makeup remover such as cleansing cream, cleansing lotion and cleansing oil, cleanser such as cleansing foam, soap and body wash, and the like.

Furthermore, the cosmetics may further contain an adjuvant commonly used in the cosmetological field such as a fat substance, an organic solvent, a solubilizer, a concentrate and a gelling agent, a softener, an anti-oxidant, a suspending agent, a stabilizer, a foaming agent, an air freshener, a surfactant, water, an ionic or non-ionic emulsifier, a filling agent, a metal ion sequestering agent and a chelating agent, a preservative, a vitamin, a blocking agent, a wetting agent, an essential oil, a dye, a pigment, a hydrophilic or lipophilic activator, a lipid follicle or any other components commonly used in the cosmetics.

Advantageous Effects

The composition for inhibiting neurotransmitter secretion according to the present disclosure has a synergistic effect related to inhibition of SNARE complex formation, and thereby, it can prevent active secretion of neurotransmitters, and thus can reduce muscle contraction to improve skin wrinkles.

BRIEF DESCRIPTION OF DRAWINGS

FIG. 1 shows the result of confirming the muscle contraction inhibition effect of each of hyperoside and quercitrin known to be contained in a *Zanthoxylum piperitum* fruit.

FIG. 2 shows the ability to inhibit electric signal transmission of the *Z. piperitum* fruit extract in a nerve cell.

FIG. 3 shows the effect of inhibiting neurotransmitter secretion of the *Z. piperitum* fruit extract.

FIG. 4 shows the evaluation of the cytotoxicity of the *Z. piperitum* fruit extract.

FIG. 5 shows the muscle paralysis efficacy of the *Z. piperitum* fruit extract.

FIG. 6 shows the synergistic effect of the *Z. piperitum* extract and argireline (acetyl hexapeptide 8).

FIG. 7 shows the muscle contraction inhibition effect upon single treatment of argireline.

FIG. 8 shows the synergistic effect of the *Z. piperitum* extract and BoNT/A LC that is a Botox effective substance.

MODE FOR INVENTION

Hereinafter, the present disclosure will be described in more detail by examples. These examples are only for describing the present disclosure in more detail, and it will be apparent to those skilled in the art to which the present disclosure pertains that the scope of the present disclosure is not limited by these examples.

EXAMPLE

1. Preparation of *Zanthoxylum piperitum* Extract and Confirmation of Effective Substance (FIG. 1)

(1) Preparation of *Zanthoxylum piperitum* Extract

*Zanthoxylum piperitum* fruits were washed, dried and pulverized, and using them, a *Z. piperitum* ethanol extract was prepared. Specifically, the ethanol extract was prepared by a method of extracting at a room temperature for 2 hours by adding 70% ethanol as an extraction solvent, and then powdering the obtained extract by filtering and concentrating.

(2) Confirmation of Effective Substance

In order to test the muscle contraction inhibition effect of each of hyperoside and quercitrin known to be contained in the *Z. piperitum* fruit, a *Caenorhabditis elegans* system was introduced. As the *Caenorhabditis elegans,* a wild-type N2strain was used, which was provided by *Caenorhabditis* Genetics Center. The *Caenorhabditis elegans* at a synchronized young-adult stage was harvested with M9 (+0.01% PEG, 0.1% DMSO) buffer and washed and spun down twice, and then diluted with a proper amount of M9 buffer and 50 ul each was distributed to an e-tube. After each compound was added, the final reaction volume was adjusted to 1 ml. After each compound was treated in an incubator at 20° C. for 1 hour, all 1 ml was transferred to a 24-well plate for video recording. In the recorded video, the number of swims per minute was calculated by measuring the number of swims for 20 seconds of 10 animals, where one round trip from the right end to the left end and back to the right end was counted as "one swim". The muscle paralysis effect was calculated by 100−(number of swims of experimental group)/(number of swims of control group)×100. The error bar was calculated by S.E.M (Standard Error of Mean) and statistical processing was performed by Student's t-test.

As the result of the experiment, the muscle contraction effect of hyperoside was incomplete, but the muscle contraction effect of quercitrin was confirmed (FIG. 1).

(3) Confirmation of Quercitrin Content

The content of quercitrin in the *Z. piperitum* ethanol extract prepared above and a *Z. piperitum* hot water extract and a *Z. piperitum* ultrasonic extract was measured. As the *Z. piperitum* hot water extract, '*Zanthoxylum piperitum* fruit extract' of BIO FD&C was used, and as the *Z. piperitum* ultrasonic extract, Jeju Chophi (*Z. piperitum* fruit extract) of The Garden of Natural Solution was used. The content of quercitrin of the ultrasonic extracted *Zanthoxylum piperitum* extract was 4 ppm, and the content of quercitrin of the hot water extract was 3 ppm, and the content of quercitrin of the ethanol extract was measured as 9 ppm, and therefore, it was confirmed that the quercitrin content was significantly increased in ethanol extraction than other solvent extraction methods. On the other hand, in 'Zanthalene' of Indena, which is the *Zanthoxylum bungeanum* extract, quercitrin was not detected (less than 1 ppm).

2. Inhibition Ability of Electric Signal Transmission in Nerve Cells (FIG. 2)

(1) Experimental Method

Using the *Zanthoxylum piperitum* fruit ethanol extract prepared above, the ability to inhibit electric signal transmission in nerve cells was measured. Specifically, to measure the change of the calcium ion inflow by KCl stimulation in a nerve cell line, NG108-15, FLIPR Calcium Assay Kit was used. The NG108-15 was aliquoted in a poly-L-lysine-coated 96-well plate so as to be $1 \times 10^4$ cells/well. At the $3^{rd}$ day after aliquoting, the *Z. piperitum* fruit extract was diluted in serum-free DMEM and treated for 1 hour. Then, a loading buffer was treated and it was cultured in a $CO_2$ incubator for 2 hours at 37° C. The loading butter contains a fluorescence substance which reacts to the calcium ion, and due to the masking dye fluorescence results only from the calcium ion in the cells. After culturing, stimulation was provided with 70 mM KCl to the cells using FlexStation and fluorescence was measured at 485/525 nm.

(2) Experimental Result

When depolarization is induced with 70 mM KCl in nerve cells, $Ca^{2+}$ flows into the cells. When the *Z. piperitum* fruit extract was treated, $Ca^{2+}$ inflow by depolarization was significantly inhibited (FIG. 2). Through this, it could be seen that the *Z. piperitum* fruit extract inhibits transmission of electric signals in nerve cells.

3. Neurotransmitter Secretion Inhibition by *Z. piperitum* Fruit Extract (FIG. 3)

(1) Experimental Method

In order to find out the change of neurotransmitter secretion under the co-culture condition of nerve cells and muscle cells, Neurotransmitter Transporter Uptake Assay Kit was used. At the $3^{rd}$ day after co-culture, dye solution was treated for 30 minutes, and then the *Z. piperitum* fruit extract prepared above was diluted in HBSS buffer (HBSS+20 mM HEPES) and treated for 30 minutes. The dye solution contained a fluorescence substance imitating neurotransmitters and a masking dye. By the masking dye, when the fluorescence substance enters the cells, fluorescence is shown, and when it is released, fluorescence disappears. After treatment, using FlexStation, the cells were stimulated with 70 mM KCl, and fluorescence was measured at 485/525 nm.

(2) Experimental Result

Whether the *Z. piperitum* fruit extract inhibits transmission of electric signals and ultimately inhibits neurotransmitter secretion was confirmed. Neurotransmitters are released from a presynaptic neuron to a synapse gap when an action potential is generated in nerve cells. The released neurotransmitters bind to a receptor of a postsynaptic neuron present in muscle to produce an action potential in a motor neuron and then signals are converted into muscle contraction. Since the environment in which the neuromuscular junction is formed is an appropriate condition to study this process, NG108-15 and C2C12 were co-cultured to create an in vitro condition to form a neuromuscular junction.

Experimental results showed that KCl treatment reduces the fluorescence value, relatively to the control group, which means that KCl treatment promotes the secretion of neurotransmitters. When the *Z. piperitum* fruit extract was treated together thereto, the secretion of neurotransmitters promoted by KCl treatment reduced (FIG. 3). Through this, it was confirmed that the *Z. piperitum* fruit extract inhibited secretion of neurotransmitters.

4. Evaluation of Cytotoxicity of *Z. piperitum* Fruit Extract (FIG. 4)

(1) Experimental Method

In order to confirm the cytotoxicity of the *Z. piperitum* fruit extract treatment concentration, cell viability was measured by MTT assay. The NG108-15 cell was aliquoted to a poly-L-lysine-coated 96-well plate so as to be $1 \times 10\ 4$ cells/well, and cultured for 24 hours and attached to the plate. Then, two substances were diluted by serum-free DMEM to each concentration and treated to the cell, and then cultured in a CO2 incubator for 4 hours. After removing the supernatant, 0.5 mg/ml MTT solution dissolved in serum-free DMEM was treated to the cell by 100 μL each and reacted for 3 hours. After the reaction, the MTT solution was removed and to dissolve a formazan crystal, isopropanol 100 μL was added and after stirring for 10 minutes absorbance was measured at 540 nm with a microplate reader.

(2) Experimental Result

It was confirmed that there was no cytotoxicity, as the cell viability of 100% or more was shown at all concentrations, when the *Z. piperitum* fruit extract was treated by 12.5, 25, 50 ppm (FIG. 4).

5. Muscle Paralysis Efficacy of *Z. piperitum* Fruit Extract (FIG. 5)

Using the *Caenorhabditis elegans* system described in the 1. (2), the muscle paralysis efficacy of the *Z. piperitum* fruit extract prepared above was tested.

As the experimental result, when the *Z. piperitum* fruit extract was treated to *Caenorhabditis elegans*, the muscle paralysis effect increased according to the concentration. In case of 0.01% *Z. piperitum* fruit extract, there was no muscle paralysis effect, but when 0.05% *Z. piperitum* fruit extract was treated, 8.5% of muscle paralysis effect was shown, and when 0.1% *Z. piperitum* fruit extract was treated, 24.1% of muscle paralysis effect was shown (FIG. 5). Through this, it was confirmed that there was muscle paralysis efficacy at a subject level when the *Z. piperitum* fruit extract was treated. In addition, based on the previous cell experiment result, it can be inferred that the *Z. piperitum* fruit extract induces paralysis of muscle by inhibiting secretion of neurotransmitters in nerve cells similarly to the Botox mechanism.

Figures 7, 8:
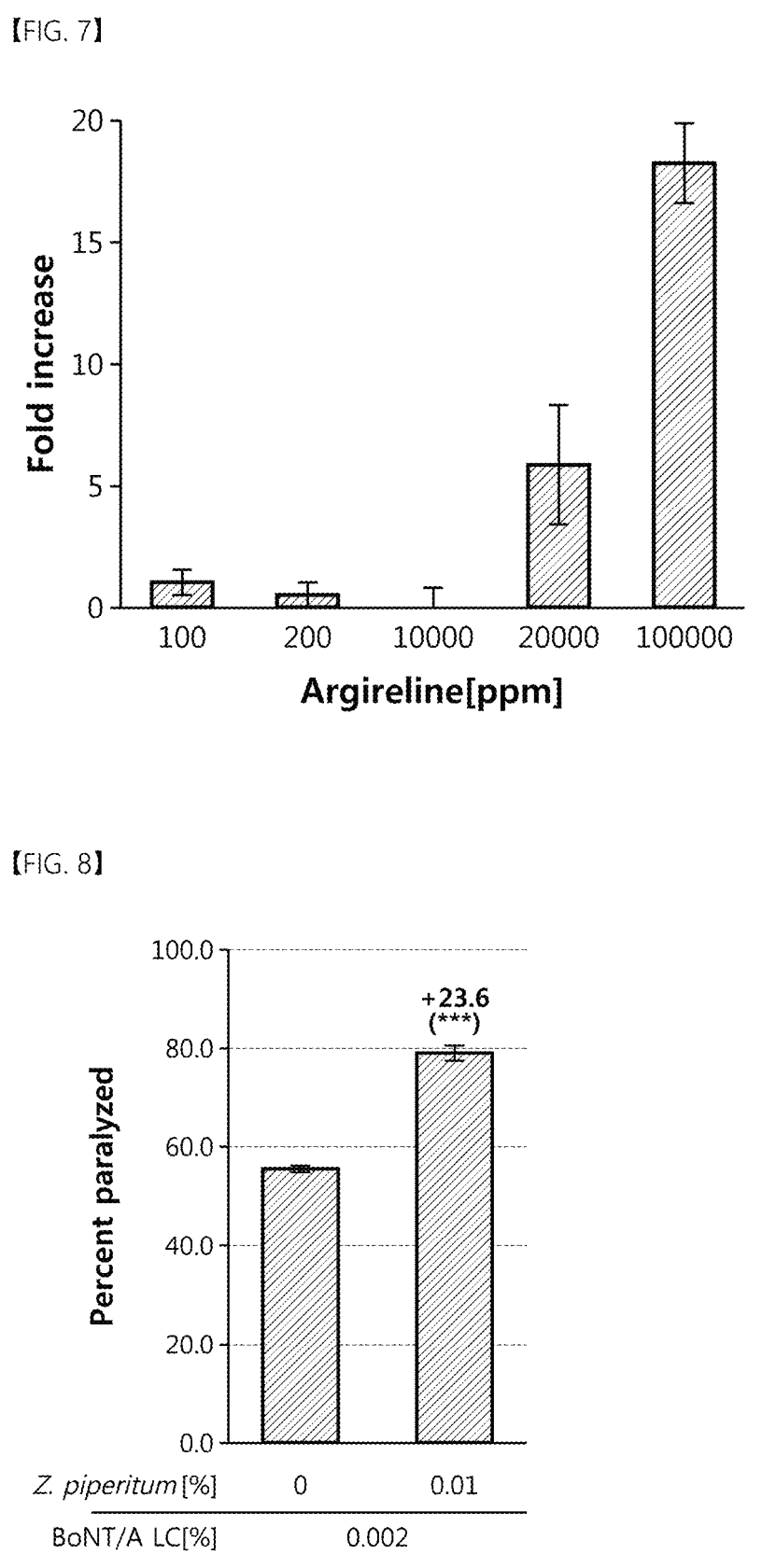

6. Synergistic Effect Test of Combination of *Z. piperitum* Fruit Extract and Argireline (FIGS. 6 and 7)

The synergistic effect between the *Z. piperitum* fruit extract and Botox efficacy materials was tested. First, a synergistic effect with argireline (acetyl hexapeptide-8) which inhibits SNARE formation by binding to SNAP-25 in nerve cells was tested.

As the experimental result, it was confirmed that the synergistic effect does not appear when the *Z. piperitum* extract was used less than argireline (Z. piperitum 50 ppm, argireline 100 ppm), and the synergistic effect appears when the Z. piperitum extract was used at least equal to or greater than argireline (FIG. 6). In addition, it was confirmed that the muscle contraction inhibition effect of argireline (100 ppm) increased about 15 times or more when used together with Z. piperitum extract 500 ppm (FIG. 6).

An experiment was performed in order to find out how much argireline is needed to achieve this amount of inhibition effect by itself. By gradually increasing the amount of the substance, it was confirmed that 100,000 ppm of argireline was needed to obtain the same level of effect as the combination of argireline 100 ppm and Z. piperitum extract 500 pp (FIG. 7).

7. Synergistic Effect Test of Combination of Z. piperitum Extract and BoNT/A LC (FIG. 8)

Next, it was tested whether the Z. piperitum fruit extract shows a synergistic effect on the effective part of the botulinum toxin. Since it is difficult to use botulinum toxin in experiments due to its severe toxicity and strict regulation, the synergistic effect was measured using a light chain region (BoNT/A LC) which is a site with enzymatic activity in the botulinum toxin protein. 0.002% (20 ppm) Treatment with BoNT/A LC alone had a muscle paralysis effect of about 50%, like the muscle paralysis effect of botulinum toxin, and through this, it can be seen that BoNT/A LC also showed Botox efficacy like botulinum toxin. To test the synergistic effect, when the 0.01% Z. piperitum fruit extract was treated to BoNT/A LC together, the synergistic effect of 20% or more was shown (FIG. 8). Through this result, it could be seen that the Z. piperitum fruit extract showed the synergistic effect throughout the materials showing Botox efficacy.

The invention claimed is:

1. A method for inhibiting neurotransmitter secretion, comprising applying a composition comprising a combination of (i) a Zanthoxylum piperitum fruit extract and (ii) a SNARE formation inhibitor as an active ingredient to a subject in need thereof,
   wherein the SNARE formation inhibitor is argireline, botulinum neurotoxin type A light chain (BoNT/A LC), or a mixture thereof, and
   wherein a weight of the comprised Zanthoxylum piperitum fruit extract is equal to or greater than a weight of the SNARE formation inhibitor.

2. The method according to claim 1, wherein the Zanthoxylum piperitum fruit extract is one or more selected from the group consisting of a squeezed juice, an ultrasonic extract, a water extract, an extract of a lower alcohol aqueous solution having 1 to 4 carbon atoms and an extract of a lower alcohol having 1 to 4 carbon atoms of a Zanthoxylum piperitum fruit.

3. The method according to claim 1, wherein the Zanthoxylum piperitum fruit extract comprises 3 to 50 ppm of quercitrin.

4. The method according to claim 1, wherein the weight of the Zanthoxylum piperitum fruit extract comprised in the total composition is equal to or greater than the weight of the SNARE formation inhibitor.

5. The method according to claim 1, wherein the composition comprises (i) 100 to 500 ppm of Zanthoxylum piperitum fruit extract and (ii) 10 to 100 ppm of SNARE formation inhibitor.

6. The method according to claim 1, wherein the method improves skin wrinkles in the subject.

7. The method according to claim 1, wherein the composition is a cosmetic.

8. The method according to claim 1, wherein the SNARE formation inhibitor is argireline.

9. The method according to claim 1, wherein the SNARE formation inhibitor is botulinum neurotoxin type A light chain (BoNT/A LC).

* * * * *